United States Patent
Ohno (10) Patent No.: US 11,382,589 B2
(45) Date of Patent: Jul. 12, 2022

(54) RADIATION IMAGE PROCESSING DEVICE AND RADIATION IMAGE PROCESSING METHOD

(71) Applicant: Shimadzu Corporation, Kyoto (JP)

(72) Inventor: Yoshinori Ohno, Kyoto (JP)

(73) Assignee: Shimadzu Corporation, Kyoto (JP)

(*) Notice: Subject to any disclaimer, the term of this patent is extended or adjusted under 35 U.S.C. 154(b) by 276 days.

(21) Appl. No.: 16/605,098

(22) PCT Filed: Apr. 20, 2017

(86) PCT No.: PCT/JP2017/015882
§ 371 (c)(1),
(2) Date: Aug. 17, 2020

(87) PCT Pub. No.: WO2018/193576
PCT Pub. Date: Oct. 25, 2018

(65) Prior Publication Data
US 2020/0375566 A1 Dec. 3, 2020

(51) Int. Cl.
*A61B 6/00* (2006.01)
*G06T 5/00* (2006.01)

(52) U.S. Cl.
CPC ............ *A61B 6/5282* (2013.01); *G06T 5/001* (2013.01); *G06T 2207/10116* (2013.01)

(58) Field of Classification Search
CPC ..... A61B 6/5282; A61B 6/4291; A61B 6/544; A61B 6/5205; G06T 5/001; G06T 5/002; G06T 2207/10116
See application file for complete search history.

(56) References Cited

U.S. PATENT DOCUMENTS

2015/0379711 A1   12/2015   Imai
2016/0235385 A1   8/2016    Enomoto et al.

FOREIGN PATENT DOCUMENTS

JP   2014-207958 A   11/2014
JP   2015-089429 A   5/2015
(Continued)

OTHER PUBLICATIONS

Fieselmann A et al, Full-field digital mammography with grid-less acquisition and software-based scatter correction, Mar. 6, 2013, SPIE, Medical Imaging 2013, 86685Y, 1-9. (Year: 2013).*
(Continued)

*Primary Examiner* — Matthew C Bella
*Assistant Examiner* — Kathleen M Broughton
(74) *Attorney, Agent, or Firm* — Muir Patent Law, PLLC (57) ABSTRACT

A radiation image processing device (100) includes an image processor (6) configured to calculate an adjustment coefficient ($I_{ideal}/I_{real}$) for adjusting a signal reduction rate ($D_{scat}$) due to removal of a scattered component in a subject (S) of radiation transmitting through the subject (S) acquired based on a luminance value ($I_{nogrid}$) of a radiation image ($X_{nogrid}$) captured with the radiation radiated to the subject (S) without a grid (8) being arranged, the luminance value ($I_{nogrid}$) of the radiation image ($X_{nogrid}$) containing a signal of a scattered ray.

7 Claims, 3 Drawing Sheets

(56) References Cited

FOREIGN PATENT DOCUMENTS

| JP | 2015181649 A | * | 10/2015 | ........... A61B 6/5282 |
|----|--------------|---|---------|-------------------------|
| JP | 2016032623 A | * | 3/2016  | ........... A61B 6/4233 |
| JP | 2016172098 A | * | 9/2016  |                         |
| JP | 2017012445 A | * | 1/2017  | ............. G06T 5/008 |

OTHER PUBLICATIONS

Lai C-J et al., Reduction in x-ray scatter and radiation dose for volume-of-interest (VOI) cone beam breast CT—a phantom study, Nov. 7, 2009, Phys Med Biol, 54(21): 6691-6709. (Year: 2009).*
Rana R et al, Anti-catter grid artifact elimination for high resolution x-ray imaging CMOS detectors, 2015, Proc SPIE Int Soc Opt Eng, 9412, 1-25 (Year: 2015).*
Written Opinion by the International Search Authority for PCT application No. PCT/JP2017/015882 (dated Jul. 18, 2017), submitted with a machine translation.

* cited by examiner

RADIATION IMAGE PROCESSING DEVICE AND RADIATION IMAGE PROCESSING METHOD

TECHNICAL FIELD

The present invention relates to a radiation image processing device and a radiation image processing method.

BACKGROUND ART

Conventionally, a radiation image processing device including an image processor (image processor) that removes signal components corresponding to scattered rays in a radiation image is disclosed. Such a radiation image processing device is disclosed in Japanese Patent Laid-Open No. 2014-207958, for example.

Conventionally, in a radiation image processing device, radiation that has entered a subject at the time of imaging is scattered (scattered rays) inside the subject such that blurring disadvantageously occurs in a captured radiation image or the contrast is disadvantageously lowered (the image quality of the radiation image is disadvantageously deteriorated). Therefore, conventionally, in order to improve the image quality of the radiation image, a grid in which lead or the like, which does not easily transmit radiation, is arranged in a grid pattern, is arranged between the subject and a detector that detects radiation such that it has been attempted to reduce the influence of the scattered rays that cause a deterioration in the image quality of the radiation image.

However, in order to properly use the grid, it is necessary to accurately match a distance between the grid and a radiation source and the orientation of the grid with respect to the radiation source. In particular, in a portable radiation imaging device, imaging is performed while a relatively heavy grid is arranged between the subject (such as a patient) and the detector, and thus the burden on a radiographer and the subject (such as a patient) is large.

In view of this, the radiation imaging device disclosed in Japanese Patent Laid-Open No. 2014-207958 has a configuration capable of removing the influence of the scattered rays as in a case in which imaging is performed actually using the grid, without using the grid. This radiation imaging device includes a characteristics acquirer that acquires virtual grid characteristics that are the virtual characteristics of the grid, and a scattered ray remover that performs a process of removing a signal caused by scattering in the subject from the radiation image actually captured without using the grid based on the virtual grid characteristics. Specifically, the virtual grid characteristics include a scattered ray transmittance etc. determined based on grid information (a grid ratio, a grid density, a grid material, etc.), subject information (an imaging site (such as an abdomen or a head) of the subject, etc.), imaging conditions (a radiation dose, an imaging distance, the type of radiation detector, etc.) at the time of acquiring the radiation image, etc. Note that the grid information, the subject information, the imaging conditions at the time of acquiring the radiation image, etc. are input to the radiation imaging device by a user. That is, the scattered ray transmittance, which is the virtual grid characteristics, is acquired in accordance with the grid information, the subject information, the imaging conditions at the time of acquiring the radiation image, etc. input by the user. Then, the specific frequency component of the radiation image is processed based on the virtual grid characteristics such that the signal caused by scattering in the subject is removed. Thus, the radiation image from which the signal caused by scattering has been removed can be obtained without using the grid.

However, in the radiation imaging device disclosed in Japanese Patent Laid-Open No. 2014-207958, the user needs to input the grid information, the subject information, the imaging conditions at the time of acquiring the radiation image, etc., and thus the burden on the user is large.

Prior Art

Patent Document

Patent Document 1: Japanese Patent Laid-Open No. 2014-207958

SUMMARY OF THE INVENTION

Problems to be Solved by the Invention

The present invention is intended to solve at least one of the above problems. The present invention aims to provide a radiation image processing device and a radiation image processing method capable of acquiring a radiation image from which scattered rays have been removed as in a case in which imaging is performed actually using a grid while reducing the burden on a user.

Means for Solving the Problems

In order to attain the aforementioned object, a radiation image processing device according to a first aspect of the present invention includes a database unit configured to store a characteristic related to a signal reduction rate due to removal of a scattered component, the scattered component being generated by radiation transmitting through a subject, and an image processor configured to calculate an adjustment coefficient for adjusting the characteristic related to the signal reduction rate of the radiation stored in the database unit, based on a luminance value of a radiation image captured with the radiation radiated to the subject without a grid being arranged during capturing the radiation image, the luminance value of the radiation image containing a signal of a scattered ray, the grid including a member for removing the scattered ray included in the radiation transmitting through the subject, and to remove a signal component of the scattered ray superimposed on the radiation image captured without the grid being arranged, based on the calculated adjustment coefficient.

In the radiation image processing device according to the first aspect of the present invention, the image processor is configured to calculate the adjustment coefficient for adjusting the characteristic related to the signal reduction rate of the radiation stored in the database unit, based on the luminance value of the radiation image captured with the radiation radiated to the subject without the grid being arranged during capturing the radiation image, the luminance value of the radiation image containing the signal of the scattered ray, the grid including the member for removing the scattered ray included in the radiation transmitting through the subject, and to remove the signal component of the scattered ray superimposed on the radiation image captured without the grid being arranged, based on the calculated adjustment coefficient. Accordingly, the adjustment coefficient calculated based on the luminance value of the actually captured radiation image can be calculated without a user inputting the grid, the subject, and the imaging conditions for acquiring the radiation image, for example. Furthermore, the calculated adjustment coefficient is used to adjust the characteristic related to the signal reduction rate due to the removal of the scattered component of the radiation, and thus the luminance value from which the signal component of the scattered ray at each pixel of the captured radiation image has been removed can be further adjusted, and the accurate luminance value adjusted based on a deviation between a theoretically obtained value and a value obtained from the actually captured radiation image can be acquired. Therefore, it is possible to acquire, without using the grid, the radiation image from which the scattered ray has been removed as in a case in which imaging is performed actually using the grid while the burden on the user (a radiographer and a patient who is the subject) is reduced.

In the aforementioned radiation image processing device according to the first aspect, the image processor is preferably configured to remove the signal component of the scattered ray superimposed on the radiation image captured without the grid being arranged, and calculate a luminance value $I_{est}$ (x, y) estimated assuming that the grid is arranged based on a following formula (1):

$$I_{est}(x, y) = I_{nogrid}(x, y) \times D_{prim} \times \frac{I_{ideal}}{I_{real}} \times D_{scat}, \quad (1)$$

$$(0 \le D_{prim} \le 1, 0 \le D_{scat} \le 1)$$

where $I_{nogrid}$ (x, y) represents a luminance value at coordinates (x, y) of the radiation image captured without the grid being arranged, the radiation image containing the signal of the scattered ray, $D_{prim}$ represents a signal reduction rate due to passage through the grid, $D_{scat}$ represents the signal reduction rate of the radiation stored in the database unit, $I_{ideal}$ represents an ideal luminance value under a specific imaging condition, and $I_{real}$ represents a luminance value based on the radiation image actually captured, and $I_{ideal}/I_{real}$ represents the adjustment coefficient. Accordingly, the luminance value $I_{est}$ (x, y) can be easily calculated based on the above formula (1).

In the aforementioned radiation image processing device according to the first aspect, the database unit is preferably configured to store a characteristic of a relationship between a thickness of the subject corresponding to a reduction rate of a luminance value of a pixel corresponding to a subject region in which the radiation transmits through the subject with respect to a luminance value of a pixel corresponding to a non-subject region in which the radiation does not transmit through the subject in the radiation image captured without the grid being arranged, and the signal reduction rate due to the removal of the scattered component, and the image processor is preferably configured to calculate the $I_{real}$ based on the characteristic of the relationship between the thickness of the subject and the signal reduction rate of the radiation stored in the database unit, and the luminance value of the radiation image actually captured. Accordingly, the approximate thickness of the subject can be acquired from the actually captured radiation image based on the luminance value of the pixel that the radiation directly enters without transmitting through the subject and the luminance value of the pixel that the radiation transmitting through the subject enters. Furthermore, the characteristic of the relationship between the thickness of the subject and the signal reduction rate of the radiation is used for the acquired approximate thickness of the subject such that the signal reduction rate of the radiation can be acquired. Therefore, the luminance value $I_{real}$ can be calculated using the signal reduction rate $D_{scat}$ of the radiation with respect to the approximate thickness of the subject actually imaged. That is, the luminance value $I_{real}$ based on the actually captured radiation image can be calculated. Furthermore, the adjustment coefficient $I_{ideal}/I_{real}$ for adjusting a deviation between the luminance value $I_{real}$ based on the actually captured radiation image and the ideal luminance value $I_{ideal}$ uniquely determined under the specific imaging condition can be acquired.

In the aforementioned radiation image processing device according to the first aspect, the image processor is preferably configured to calculate the $D_{prim}$ based on a ratio of a luminance value of the non-subject region in the radiation image captured in advance with the grid being arranged to a luminance value of the non-subject region in the radiation image captured without the grid being arranged. Accordingly, the value of $D_{prim}$, which is the signal reduction rate due to the passage of the radiation through the grid, can be automatically obtained based on the image actually captured without the user input. Consequently, it is possible to save the trouble of inputting.

In the aforementioned radiation image processing device according to the first aspect, the image processor is preferably configured to calculate the $D_{scat}$ based on a ratio of a luminance value of each pixel to a luminance value of the non-subject region in the radiation image captured without the grid being arranged. Accordingly, the value of $D_{scat}$, which is the signal reduction rate due to the removal of the scattered component in the subject, can be automatically obtained based on the radiation image actually captured without the user input. Consequently, it is possible to save the trouble of inputting.

In the aforementioned radiation image processing device according to the first aspect, the image processor is preferably configured to calculate a subject thickness index corresponding to the thickness of the subject based on a following formula (2):

$$\left(1 - \frac{I_{nogrid}(x, y)}{I_{nogrid}(\text{air})}\right) \quad (2)$$

where $I_{nogrid}$ (air) represents the luminance value of the non-subject region in the radiation image captured without the grid being arranged. Accordingly, the subject thickness index corresponding to the thickness of the subject can be easily acquired from the radiation image (pixel luminance value) without measuring the actual thickness of the subject.

A radiation image processing method according to a second aspect of the present invention includes calculating a coefficient representing a decrease in a signal intensity of radiation due to scattering in a subject when it transmits through the subject, based on a luminance value of a radiation image captured with the radiation radiated to the subject without a lattice-shaped grid being arranged during capturing the radiation image, in which a member for shielding a scattered ray in order to remove the scattered ray included in the radiation transmitting through the subject and a member for transmitting the radiation other than the scattered ray are alternately arranged, the luminance value of the radiation image containing a signal of the scattered ray, and a luminance value of the radiation image from which the scattered ray has been removed, the luminance value of the radiation image being acquired in advance with the grid being arranged, and removing a signal component corresponding to the scattered ray in the radiation image based on the coefficient that has been calculated by the step of calculating the coefficient.

In order to attain the aforementioned object, the radiation image processing method according to the second aspect of the present invention includes storing a characteristic related to a signal reduction rate due to removal of a scattered component, the scattered component being generated by radiation transmitting through a subject, calculating an adjustment coefficient for adjusting the characteristic related to the signal reduction rate of the radiation, based on a luminance value of a radiation image captured with the radiation radiated to the subject without a grid being arranged during capturing the radiation image, the luminance value of the radiation image containing a signal of a scattered ray, the grid including a member for removing the scattered ray included in the radiation transmitting through the subject, and removing a signal component of the scattered ray superimposed on the radiation image captured without the grid being arranged, based on the calculated adjustment coefficient.

The radiation image processing method according to the second aspect of the present invention includes calculating the adjustment coefficient for adjusting the characteristic related to the signal reduction rate of the radiation stored in a database unit, based on the luminance value of the radiation image captured with the radiation radiated to the subject without the grid being arranged during capturing the radiation image, the luminance value of the radiation image containing the signal of the scattered ray, the grid including the member for removing the scattered ray included in the radiation transmitting through the subject, and removing the signal component of the scattered ray superimposed on the radiation image captured without the grid being arranged, based on the calculated adjustment coefficient. Accordingly, in the step of calculating the adjustment coefficient, the adjustment coefficient can be calculated based on the luminance value of the actually captured radiation image without a user inputting the grid, the subject, and the imaging conditions for acquiring the radiation image, for example. Furthermore, in the step of removing the signal component of the scattered ray, the calculated adjustment coefficient is used to adjust the characteristic related to the signal reduction rate due to the removal of the scattered component of the radiation, and thus the luminance value from which the signal component of the scattered ray at each pixel of the captured radiation image has been removed can be further adjusted, and the accurate luminance value adjusted based on a deviation between a theoretically obtained value and a value obtained from the actually captured radiation image can be acquired. Therefore, it is possible to provide the radiation image processing method capable of acquiring, without using the grid, the radiation image from which the scattered ray has been removed as in a case in which imaging is performed actually using the grid while the burden on the user is reduced by the above process.

Effect of the Invention

According to the present invention, as described above, it is possible to significantly reduce or prevent light interference in the surface film that protects the light receiving surface.

MODES FOR CARRYING OUT THE INVENTION

An embodiment embodying the present invention is hereinafter described on the basis of the drawings.

[Embodiment]

The configuration of a radiation imager 101 using a radiation image processing device 100 according to the embodiment of the present invention is now described with reference to FIGS. 1 to 5.

(Overall Configuration)

Figure 1:
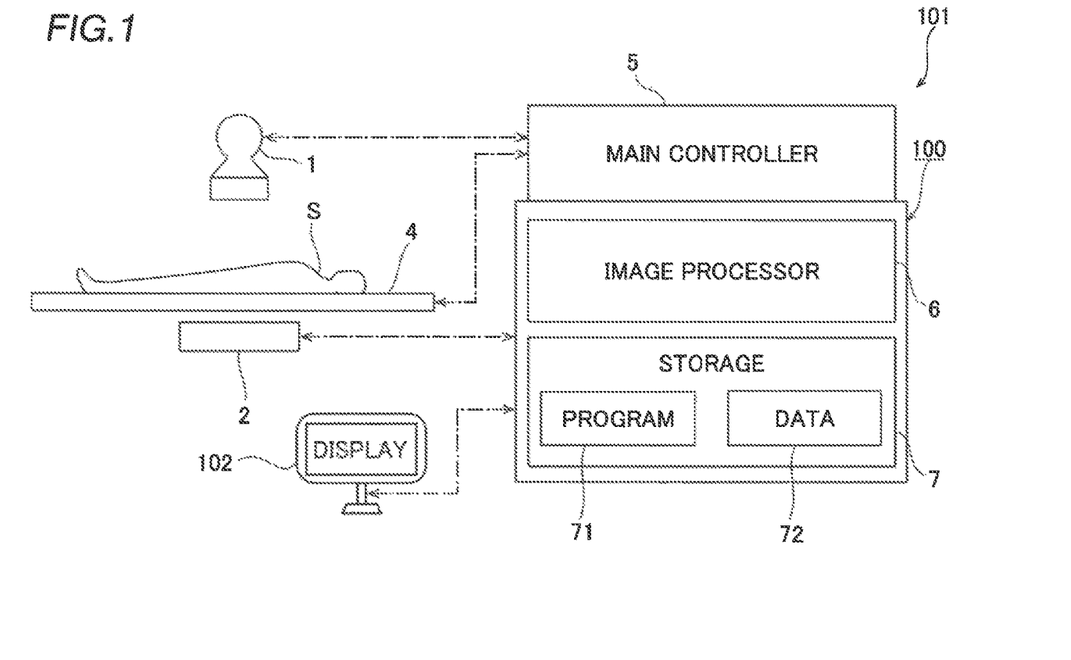
FIG. 1 is a block diagram showing the overall configuration of a radiation image processing device according to an embodiment.

First, the overall configuration of the radiation imager 101 is described based on FIG. 1. As shown in FIG. 1, the radiation imager 101 includes a radiation irradiator 1, a radiation detector 2, a placement table 4, a main controller 5, a display 102, and the radiation image processing device 100.

The placement table 4 is configured such that a subject S (a patient, for example) can be placed thereon.

The radiation irradiator 1 includes an X-ray tube, for example. Furthermore, the radiation irradiator 1 is configured to generate radiation (X-rays) when a tube voltage is applied thereto and irradiate the subject S with the radiation. The radiation detector 2 includes a flat panel detector (FPD), for example. Furthermore, the radiation detector 2 is configured to detect the radiation that has passed through the subject S, for example, and has been incident thereon, and output a signal based on the intensity of the radiation that has been incident on each pixel.

The main controller 5 includes an information processor such as a personal computer (PC). Furthermore, the main controller 5 is configured to be able to control the irradiation intensity of the radiation by the radiation irradiator 1.

The display 102 is configured to display information or the like required to operate the radiation imager 101 and the radiation image processing device 100 in addition to a captured radiation image, for example.

The radiation image processing device 100 includes an image processor 6 and a storage 7. The storage 7 is an example of a "database unit" in the claims.

The image processor 6 includes, as a dedicated information processor for image processing, an information processor such as a central processing unit (CPU). Furthermore, the image processor 6 is configured to acquire a coefficient used to acquire a radiation image by processing the signal (pixel luminance value) output from the radiation detector 2. In addition, the image processor 6 is configured to perform an image process based on the signal output from the radiation detector 2 and the coefficient acquired by the image processor 6, and acquire a radiation image $X_{est}$ estimated assuming that a grid 8 (described below) is arranged. The image processor 6 may not be provided separately from the main controller 5, and may function as an image processor 6 by causing the same CPU as the main controller 5 to execute an image processing program. A specific process of the image processor 6 is described below.

The storage 7 includes a hard disk drive (HDD), a memory, etc., and stores a program 71 executed by the image processor 6, a correspondence relationship between the thickness of the subject and the scattered dose acquired from a signal reduction rate (described below), a signal output from the radiation detector 2, data 72 such as a radiation image output from the image processor 6, etc.

(Scattered Ray Removal Process)

A scattered ray removal process to change a radiation image $X_{nogrid}$ captured without the grid 8 (see FIG. 2) being arranged and including signal components of scattered rays to the radiation image $X_{est}$ from which the signal components of the scattered rays have been removed is now described based on FIGS. 2 to 5. The scattered ray removal process is an example of a "radiation image processing method" in the claims.

Figure 2:
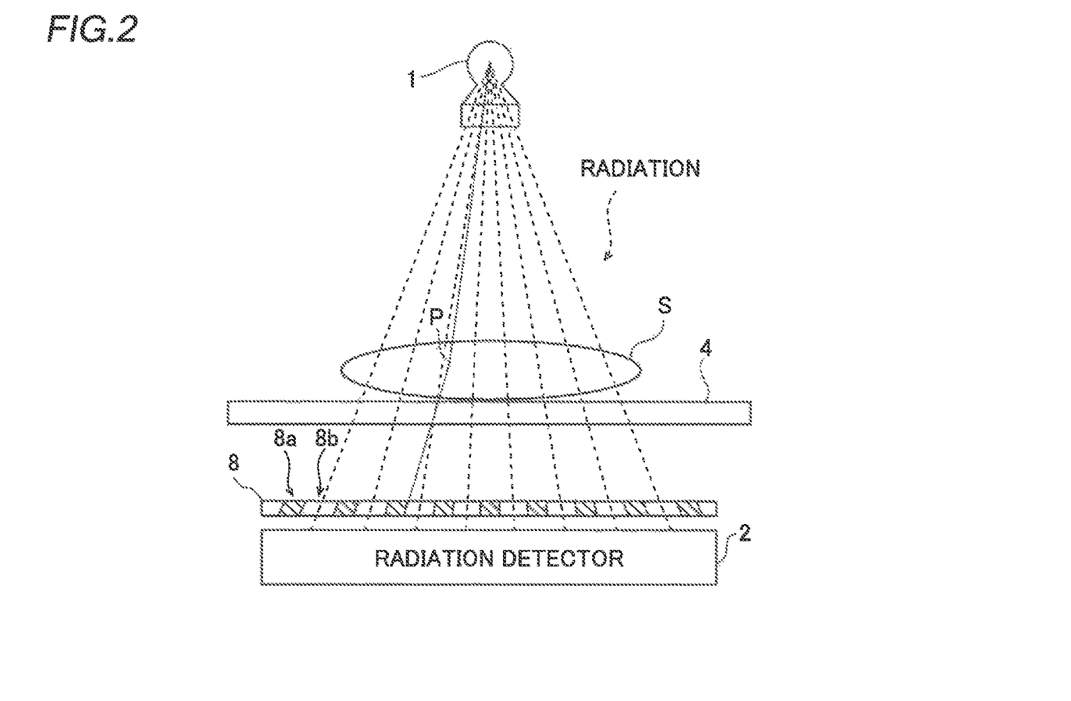
FIG. 2 is a diagram for illustrating a grid according to the embodiment.

First, the grid 8 is described briefly. As shown in FIG. 2, the grid 8 includes a plurality of shields 8a that are members for shielding scattered rays and a plurality of transmitters 8b that are members for transmitting radiation other than scattered rays. The shields 8a and the plurality of transmitters 8b of the grid 8 are formed so as to extend toward the radiation irradiator 1, and are alternately arranged, for example. The members for shielding scattered rays are made of lead, for example. The members for transmitting radiation other than scattered rays are made of aluminum, for example.

When the grid 8 is arranged between the subject S and the radiation detector 2 to remove scattered rays and a radiation image is captured, the directions of the scattered rays (radiation scattered in the subject S) are changed to a direction that intersects with a direction in which the shields 8a extend, and thus the scattered rays are incident on the shields 8a, are absorbed by the shields 8a without passing through the grid 8, and are shielded (radiation P, for example). Therefore, most of the scattered rays are removed without passing through the grid 8. On the other hand, the direction of the radiation transmitting without being scattered in the subject S is the same as the direction in which the transmitters 8b and the shields 8a extend, and thus the radiation other than the scattered rays passes through the grid 8 by passing through the transmitters 8b (although part of the radiation radiated toward the shields 8a is removed). That is, it is possible to shield scattered rays by arranging the grid 8.

In the radiation image processing device 100, an image process is performed on the radiation image $X_{nogrid}$ captured without arranging the grid 8 based on the luminance value $I_{nogrid}$ of the radiation image $X_{nogrid}$ such that it is possible to acquire the radiation image $X_{est}$ in which signal components corresponding to scattered rays have been removed (corrected) as in a case in which the grid 8 is arranged. In addition, it is possible to compare an image captured with the grid 8 being arranged in the past with an image captured without the grid 8 being arranged under substantially the same conditions.

In this embodiment, the radiation image processing device 100 includes the storage 7 that stores the characteristics related to a signal reduction rate $D_{scat}$ of radiation due to scattered rays generated by the radiation passing through the subject S, and the image processor 6 that calculates an adjustment coefficient $I_{ideal}/I_{real}$ for adjusting the characteristics related to the signal reduction rate $D_{scat}$ of radiation stored in the storage 7, based on the luminance value of the radiation image $X_{nogrid}$ captured with radiation radiated to the subject S without the grid 8 being arranged during capturing the radiation image, the luminance value of the radiation image $X_{nogrid}$ containing signals of scattered rays, the grid 8 including the members for removing scattered rays included in the radiation transmitting through the subject S, and removes signal components of the scattered rays superimposed on the radiation image $X_{nogrid}$ captured without the grid 8 being arranged based on the calculated adjustment coefficient $I_{ideal}/I_{real}$.

Specifically, the image processor 6 acquires some characteristics (described below) for calculating $D_{scat}$ from the luminance value $I_{nogrid}$ of the radiation image $X_{nogrid}$ captured without the grid 8 being arranged, and a relationship (described below) for calculating the adjustment coefficient $I_{ideal}/I_{real}$ from the storage 7. Then, the luminance value $I_{nogrid}$ is processed such that the signal reduction rate $D_{scat}$ representing a reduction in the signal intensity of radiation due to scattering in the subject S and the adjustment coefficient $I_{ideal}/I_{real}$ for adjusting $D_{scat}$ are acquired. Then, the image processor 6 acquires the luminance value $I_{est}$ of each pixel estimated assuming that signal components of scattered rays have been removed from the radiation image $X_{nogrid}$ based on the acquired $D_{scat}$ and $I_{ideal}/I_{real}$, and acquires the radiation image $X_{est}$, from which scattered rays have been removed, equivalent to a case in which imaging is performed with the grid 8 being arranged.

In this embodiment, the image processor 6 is configured to remove the signal components of the scattered rays superimposed on the radiation image $X_{nogrid}$ captured without the grid 8 being arranged, and calculate the luminance value $I_{est}(x, y)$ estimated assuming that the grid is arranged based on the following formula (3).

[Formula 3]

$$I_{est}(x, y) = I_{nogrid}(x, y) \times D_{prim} \times \frac{I_{ideal}}{I_{real}} \times D_{scat}(x, y), \quad (3)$$

$$(0 \leq D_{prim} \leq 1, 0 \leq D_{scat} \leq 1)$$

Thus, the luminance value $I_{est}(x, y)$ can be easily calculated based on the above formula (3). Here, $I_{nogrid}(x, y)$ represents a luminance value at the coordinates (x, y) of a radiation image including signals of scattered rays, which is captured without the grid being arranged, $D_{prim}$ represents a signal reduction rate due to passing through the grid, $D_{scat}$ represents a signal reduction rate of radiation stored in the storage 7, $I_{ideal}$ represents an ideal luminance value under a specific imaging condition, and $I_{real}$ represents a luminance value based on an actually captured radiation image.

Specifically, $I_{nogrid}(x, y)$ represents a luminance value at each pixel (the coordinates (x, y)) of the radiation image $X_{nogrid}$ actually captured without the grid being arranged. In addition, $D_{prim}$ represents a ratio at which the signal intensity (luminance value) is reduced by absorption by the transmitters 8b when radiation other than scattered rays passes through the transmitters 8b (members for transmitting radiation) of the arranged grid 8. Furthermore, $D_{scat}$ represents a ratio at which the signal intensity (luminance value) is reduced due to scattering of radiated radiation in the subject S. $I_{ideal}$, $I_{real}$, and an adjustment coefficient $I_{ideal}/I_{real}$ are described below.

In this embodiment, the image processor 6 is configured to calculate $D_{prim}$ based on a ratio of the luminance value $I_{grid}$ (air) of a non-subject region in the radiation image $X_{grid}$ captured in advance with the grid 8 being arranged to the luminance value $I_{nogrid}$ (air) of a non-subject region in the radiation image $X_{nogrid}$ captured without the grid 8 being arranged.

Specifically, the luminance values $I_{grid}$ (air) and $I_{nogrid}$ (air) of the pixel in the non-subject region corresponding to the detection intensity of radiation that does not transmit through (escapes from) the subject S and enters the radiation detector 2 are not affected by scattering by the subject S. The luminance value $I_{grid}$ (air) of the radiation image captured with the grid 8 being arranged is absorbed by the members forming the transmitters 8b when radiation passes through the transmitters 8b of the grid 8. Therefore, the signal reduction rate $D_{prim}$ due to absorption by the grid 8 is expressed by the following formula (4).

[Formula 4]

$$D_{prim} = \frac{I_{grid}(\text{air})}{I_{nogrid}(\text{air})}, (0 \leq D_{prim} \leq 1) \quad (4)$$

$D_{prim}$ is common in the entire radiation image $X_{nogrid}$ (all pixels), and is a value that does not depend on the coordinates (x, y).

$I_{grid}$ (air) ($I_{nogrid}$ (air)) in the non-subject region represents the luminance value of the pixel in the non-subject region corresponding to the intensity of radiation that does not transmit through (escapes from) the subject S and directly enters the radiation detector 2. Therefore, the region has the highest luminance value in an entire image. Accordingly, the image processor 6 is configured to acquire $I_{grid}$ (air) ($I_{nogrid}$ (air)) by regarding a region of an image in which the luminance value exceeds a predetermined threshold as a non-subject region in which radiation directly enters the radiation detector 2 without entering the subject S (without a loss) and averaging luminance values $I_{grid}$(x, y) (x, y)) that exceed the threshold, for example. Averaging is performed in this manner such that it is possible to significantly reduce or prevent a variation in the luminance value due to the intensity unevenness of radiation (X-rays) radiated from the radiation irradiator 1. The radiation image $X_{grid}$ acquired in advance with the grid 8 being arranged requires only the luminance value of the non-subject region, and thus imaging may be performed in a state in which the subject S is not placed.

In this embodiment, the image processor 6 is configured to calculate $D_{scat}$ (x, y) based on a ratio of the luminance value $I_{nogrid}$ (x, y) of each pixel to the luminance value $I_{nogrid}$ (air) of the non-subject region in the radiation image $X_{nogrid}$ captured without the grid 8 being arranged.

Figure 3:
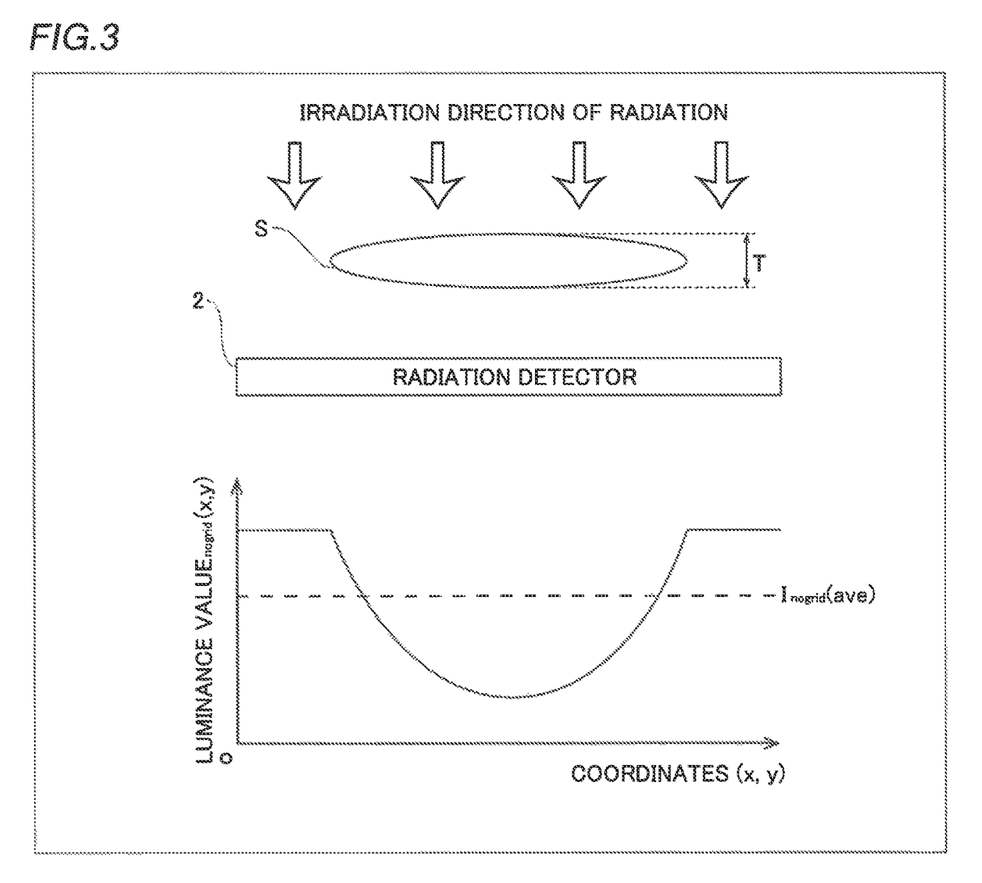
FIG. 3 is an example of a graph showing a relationship between a subject and a luminance value according to the embodiment.

Specifically, as described above, the luminance value $I_{nogrid}$ (x, y) is associated with the thickness T of the subject S at the coordinates (x, y) in the captured image (see FIG. 3). The thickness T of the subject S can be acquired based on how much the signal line is lowered due to scattering in the subject S. That is, the thickness T (x, y) of the subject S can be obtained from the ratio of the luminance value $I_{nogrid}$ (x, y) at the incident position of radiation that has passed through the subject to the luminance value $I_{nogrid}$ (air) of the non-subject region.

The signal reduction rate $D_{scat}$ (x, y) due to removal of scattered components in the subject S is associated with the thickness T (x, y) of the subject S. That is, $D_{scat}$ (x, y) is expressed by the following formula (5) based on the ratio of $I_{nogrid}$ (x, y) to $I_{nogrid}$ (air).

[Formula 5]

$$D_{scat}(x, y) = f\left(\frac{I_{nogrid}(x, y)}{I_{nogrid}(\text{air})}\right), (0 \leq D_{scat} \leq 1) \quad (5)$$

where f is some function. Note that $D_{scat}$ (x, y) is different for each pixel, and is a value that depends on the coordinates.

The characteristics data (data 72) stored in the storage 7 holds in advance the general characteristics of the ratio of $I_{nogrid}$ (x, y) to $I_{nogrid}$ (air), which is a rate of change in luminance value from the non-subject region, and the signal reduction rate $D_{scat}$ (x, y) due to removal of scattered components in the subject S. Therefore, the image processor 6 calculates (acquires) $D_{scat}$ (x, y) that matches the characteristics data.

In this embodiment, the image processor 6 is configured to calculate a subject thickness index α corresponding to the thickness T of the subject S based on the following formula (6).

[Formula 6]

$$\alpha(x, y) = \left(1 - \frac{I_{nogrid}(x, y)}{I_{nogrid}(\text{air})}\right) \quad (6)$$

Specifically, the subject thickness index α is a value normalized by dividing a difference (reduction amount) between the luminance value $I_{nogrid}$ (air) at the position of the pixel that radiation not transmitting through the subject S directly reaches and the luminance value $I_{nogrid}$ (x, y) at the coordinates (x, y) corresponding to an arbitrary position including the position of the pixel that radiation transmitting through the subject S reaches in the radiation image $X_{nogrid}$ by the luminance value $I_{nogrid}$ (air) in the case of radiation that does not transmit through the subject S and directly reaches a pixel. The subject thickness index α (x, y) is a value that differs depending on each pair of coordinates (x, y), and is an approximate value of the thickness T (x, y) of a portion of the subject S corresponding to the coordinates (x, y) represented by the luminance value $I_{nogrid}$ (x, y).

It is approximated that the thickness T (x, y) of the subject is substantially proportional to the subject thickness index α (x, y) such that it is expressed by the following formula (7).

[Formula 7]

$$T(x, y) \cong c \times \alpha(x, y) = c \times \left(1 - \frac{I_{nogrid}(x, y)}{I_{nogrid}(\text{air})}\right) \quad (7)$$

where c represents a positive proportional constant.

The signal reduction rate due to radiation scattering in the subject S can also be calculated based on the subject thickness index α (x, y). The subject thickness index α (x, y) is expressed by the following formula (8).

[Formula 8]

$$D_{scat}(x, y) = g(\alpha(x, y)) = g\left(1 - \frac{I_{nogrid}(x, y)}{I_{nogrid}(\text{air})}\right) \quad (8)$$

where g represents some function.

In this embodiment, the storage 7 is configured to store the characteristics of a relationship between the thickness T of the subject S corresponding to the reduction rate of the luminance value $I_{nogrid}$ (x, y) of the pixel corresponding to a subject region in which radiation transmits through the subject S with respect to the luminance value $I_{nogrid}$ (air) of the pixel corresponding to the non-subject region in which radiation does not transmit through the subject S in the radiation image $X_{nogrid}$ captured without the grid 8 being arranged, and the signal reduction rate $D_{scat}$ of radiation due to scattered rays. The image processor 6 is configured to calculate heal based on the signal reduction rate $D_{scat}$ (x, y) obtained from the characteristics of the relationship between the thickness T of the subject S and the subject thickness index α (x, y), which is the signal reduction rate of radiation, stored in the storage 7 and the luminance value $I_{nogrid}$ of the radiation image $X_{nogrid}$ actually captured.

Specifically, the luminance values $I_{nogrid}$ (x, y) of the entire radiation image $X_{nogrid}$ (or the entire subject region) are averaged such that a luminance value $I_{nogrid}$ (ave) (which is an average value) in a case in which the subject S having a uniform composition and thickness T in the entire radiation image $X_{nogrid}$ is considered to be imaged can be acquired (see FIG. 3). Then, $I_{nogrid}$ (ave) is substituted into the following formula (9) such that $I_{real}$, which is an average value of estimated values based on the actual imaging data $X_{nogrid}$ in a case in which the grid 8 is assumed to be arranged, can be acquired.

[Formula 9]

$$I_{real} = I_{nogrid}(\text{ave}) \times D_{prim} \times D_{scat}(\text{ave}), (0 \le D_{prim} \le 1, 0 \le D_{scat} \le 1) \quad (9)$$

Figure 4:
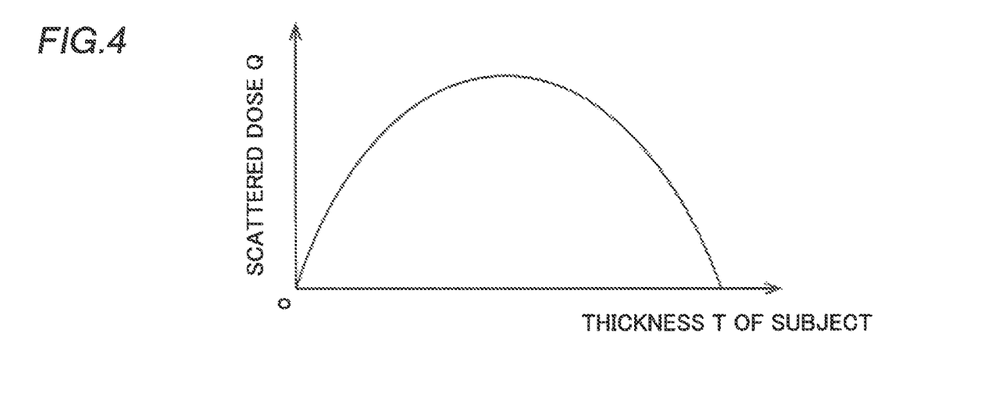
FIG. 4 is an example of a graph showing a relationship between the thickness of the subject and the scattered dose according to the embodiment.

As described above, the scattered dose Q of radiation that passes through the subject S changes in association with the thickness T of the subject S (see FIG. 4). Specifically, the scattered dose Q increases as the thickness T increases while the thickness T of the subject S is relatively small. However, when the thickness T of the subject S increases to some extent, due to a decrease in the amount of radiation itself that can reach the radiation detector 2 without being scattered, the scattered dose Q decreases as the thickness T increases. That is, as shown in FIG. 4, the scattered dose Q is shown by a mountain-shaped (upward convex) graph that changes from increasing to decreasing as the thickness T increases. Such a correspondence relationship between the thickness T of the subject S and the scattered dose Q is acquired in advance such that a scattered dose Q (x, y) at the corresponding position can be acquired from the thickness T (x, y) of the subject S at coordinates where each pixel is located. The correspondence relationship between the thickness T of the subject and the scattered dose Q is stored in the storage 7.

The approximate thickness T (ave) of the subject S can be obtained based on the above-described correspondence relationship based on the specific imaging conditions stored in the storage 7 from the above-described average luminance value $I_{nogrid}$ (ave) in a case in which the subject S is considered to be uniform. That is, the scattered dose Q theoretically derived from the approximate thickness T (ave) under the ideal conditions is acquired, and thus a luminance value $I_{ideal}$ can be acquired from the acquired scattered dose Q. The correspondence relationship between the scattered dose Q and the thickness T used to acquire $I_{ideal}$ is a correspondence relationship under the ideal conditions. Therefore, due to the unknown imaging conditions of the shields 8a (information about the grid 8 (a grid ratio, a grid density, a grid material, the focusing distances of the shields 8a, etc.), for example), a deviation due to a difference between the density of the subject S used to obtain the characteristics and the density of the subject S to be actually imaged, or an error caused by another cause, for example, $I_{ideal}$ may deviate from the actual value. Thus, the value of $D_{scat}$, which is also theoretically obtained, is adjusted by multiplication by the adjustment coefficient $I_{ideal}/I_{real}$ which is a ratio (difference) of $I_{ideal}$ theoretically obtained under the ideal conditions to $I_{real}$ that is an average value of estimated values based on the actual imaging data $X_{nogrid}$ such that an accurate calculation result in which the deviation has been adjusted can be obtained.

The correspondence relationship between the scattered dose Q and the thickness T used to acquire $I_{ideal}$ is acquired from a correspondence relationship in which a relationship between the thickness T of the subject S (such as an acrylic plate) and the scattered dose Q obtained from the detected luminance value is measured in advance, using an acrylic plate or a phantom (human phantom) as the subject S, for example, and is stored as a data table in the storage 7.

By multiplication by the adjustment coefficient $I_{ideal}/I_{real}$ acquired based on the theoretically obtained value $I_{ideal}$ that is obtained in this manner and holds under the ideal conditions and $I_{real}$ obtained based on the characteristics data (actual measurement data), the signal reduction rate $D_{scat}$ due to removal of scattered components can be adjusted. That is, $D_{scat}$ is multiplied by the adjustment coefficient $I_{ideal}/I_{real}$ such that it is possible to deal with a case in which a deviation or error of a positional relationship between the radiation irradiator 1 and the radiation detector 2 occurs and a case in which the imaging conditions are unknown (a case in which the imaging conditions cannot be set correctly) by performing adjustment from a theoretically calculated value ($D_{scat}$ not multiplied by the adjustment coefficient) at the time of actual imaging (at the time of capturing the radiation image $X_{nogrid}$).

Figure 5:
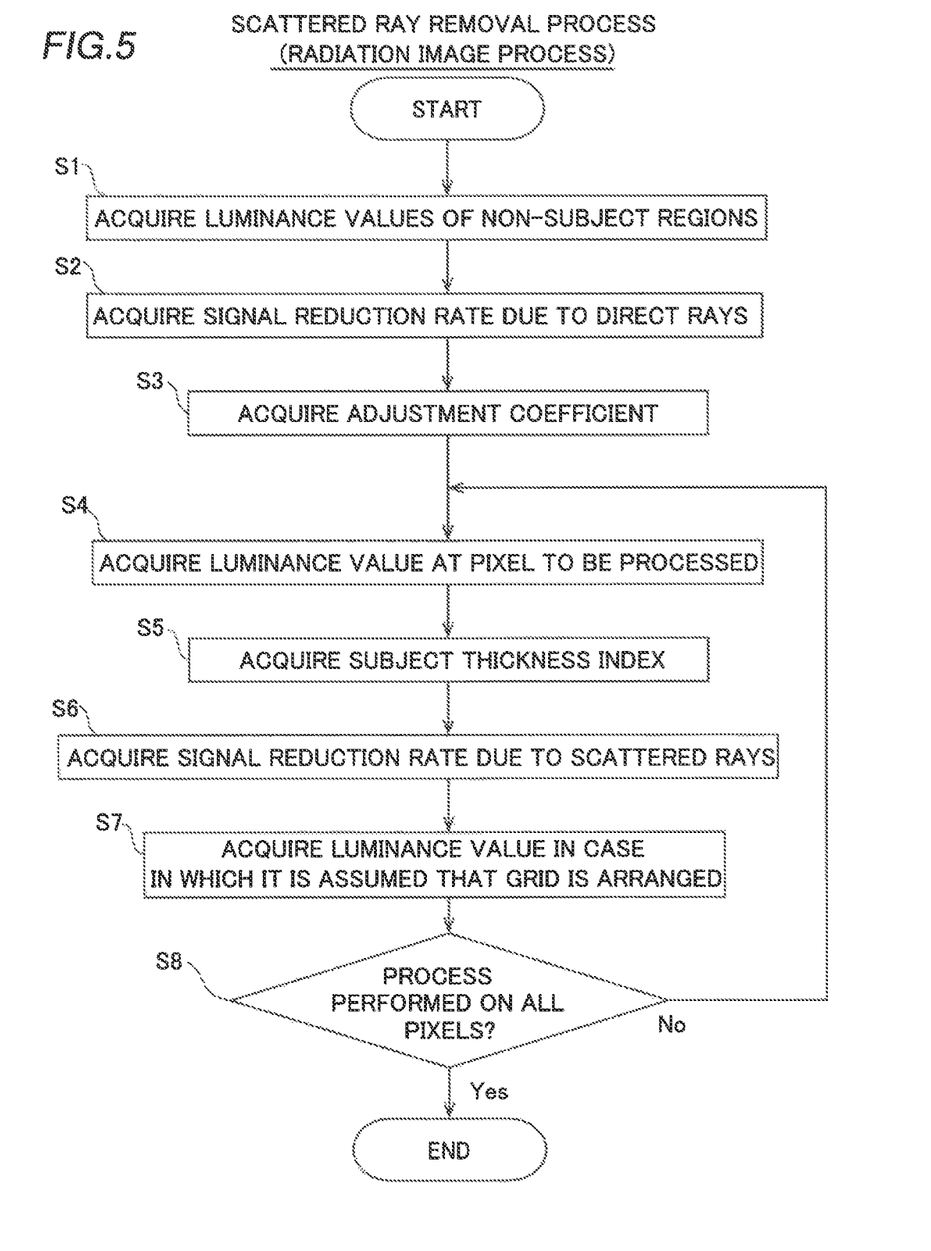
FIG. 5 is a flowchart of a scattered ray removal process according to the embodiment.

The procedure of the scattered ray removal process is now described along a flowchart based on FIG. 5.

When the scattered ray removal process is started for the radiation image $X_{nogrid}$ captured without the grid 8 being arranged, the process advances to step S1. In step S1, the luminance value $I_{grid}$ (air) of the non-subject region of the radiation image $X_{grid}$ captured with the grid 8 being arranged, which is acquired (measured) in advance, and the luminance value $I_{nogrid}$ (air) of the non-subject region of the radiation image $X_{nogrid}$ captured without the grid 8 being arranged to be processed are acquired, and the process advances to step S2. Note that the luminance value $I_{grid}$ (air) and the characteristics (such as the relationship between $D_{scat}$ and thickness T) related to the signal reduction rate due to removal of scattered components are stored in the storage 7 before the start of the scattered ray removal process.

In step S2, $D_{prim}$, which is the signal reduction rate of direct rays, is acquired based on $I_{grid}$ (air) and $I_{nogrid}$ (air), and the process advances to step S3.

In step S3, $I_{real}$ and $I_{ideal}$ are acquired from the average luminance value $I_{nogrid}$ (ave) of the radiation image $X_{nogrid}$, the characteristics data, and the relationship between the thickness T of the subject S and the scattered dose Q, for example. Then, the adjustment coefficient $I_{ideal}/I_{real}$ is acquired, and the process advances to step S4.

In step S4, the luminance value $I_{nogrid}$ (x, y) at the pixel (coordinates) to be processed in $X_{nogrid}$ is acquired, and the process advances to step S5.

In step S5, the subject thickness index $\alpha$ (x, y) at the pixel to be processed is acquired based on $I_{nogrid}$ (x, y) and $I_{nogrid}$ (air), and the process advances to step S6.

In step S6, the signal reduction rate $D_{scat}$ due to removal of scattered components in the subject is acquired based on the subject thickness index $\alpha$ (x, y) (or the luminance value change ratio $I_{nogrid}$ (x, y)/$I_{nogrid}$ (air)), and the process advances to step S7.

In step S7, based on the above formula (3), the luminance value of the pixel to be processed is processed, and the virtual luminance value $I_{est}$ (x, y) estimated assuming that the grid is arranged is acquired. Then, the process advances to step S8.

In step S8, when the process has not been performed on all the pixels (No), the process returns to step S4, and when the process has been performed on all the pixels (Yes), the scattered ray removal process is terminated.

[Advantages of Embodiment]

According to this embodiment, the following advantages are obtained.

According to this embodiment, as described above, the image processor 6 is configured to calculate the adjustment coefficient $I_{ideal}/I_{real}$ for adjusting the characteristics related to the signal reduction rate $D_{scat}$ of radiation stored in the storage 7, based on the luminance value $I_{nogrid}$ of the radiation image $X_{nogrid}$ captured with radiation radiated to the subject S without the grid 8 being arranged during capturing the radiation image $X_{nogrid}$, the luminance value $I_{nogrid}$ of the radiation image $X_{nogrid}$ containing signals of scattered rays, the grid 8 including the members for removing scattered rays included in the radiation transmitting through the subject S, and remove the signal components of the scattered rays superimposed on the radiation image $X_{nogrid}$ captured without the grid 8 being arranged based on the calculated adjustment coefficient $I_{ideal}/I_{real}$. Accordingly, the adjustment coefficient $I_{ideal}/I_{real}$ calculated based on the luminance value of the actually captured radiation image can be calculated without a user inputting the grid 8, the subject S, and the imaging conditions for acquiring the radiation image $X_{nogrid}$, for example. Furthermore, the calculated adjustment coefficient $I_{ideal}/I_{real}$ is used to adjust the characteristics related to the signal reduction rate $D_{scat}$ due to removal of scattered components of radiation, and thus the luminance value from which the signal components of the scattered rays at each pixel of the captured radiation image $X_{nogrid}$ have been removed can be further adjusted, and the accurate luminance value $I_{est}$ adjusted based on the deviation between the theoretically obtained value and the value obtained from the actually captured radiation image $X_{nogrid}$ can be acquired. Therefore, it is possible to acquire, without using the grid 8, the radiation image $X_{est}$ from which scattered rays have been removed as in a case in which imaging is performed actually using the grid 8 while the burden on the user (a radiographer and a patient who is the subject S) is reduced.

According to this embodiment, as described above, the image processor 6 is configured to remove the signal components of the scattered rays superimposed on the radiation image $X_{nogrid}$ captured without the grid 8 being arranged and calculate the luminance value $I_{est}$ (x, y) estimated assuming that the grid 8 is arranged based on the above formula (3). Accordingly, the luminance value $I_{est}$ (x, y) can be easily calculated based on the above formula (3).

According to this embodiment, as described above, the storage 7 is configured to store the characteristics of the relationship between the thickness T of the subject S corresponding to the reduction rate of the luminance value $I_{nogrid}$ (x, y) of the pixel corresponding to the subject region in which radiation transmits through the subject S with respect to the luminance value $I_{nogrid}$ (air) of the pixel corresponding to the non-subject region in which radiation does not transmit through the subject S in the radiation image $X_{nogrid}$ captured without the grid 8 being arranged, and the signal reduction rate $D_{scat}$ of radiation due to scattered rays. The image processor 6 is configured to calculate $I_{real}$ based on the characteristics of the relationship between the thickness T of the subject S and the subject thickness index $\alpha$ (x, y), which is the signal reduction rate of radiation, stored in the storage 7 and the luminance value $I_{nogrid}$ of the radiation image $X_{nogrid}$ actually captured. Accordingly, the approximate thickness T (ave) of the subject S can be acquired from the actually captured radiation image $X_{nogrid}$ based on the luminance value $I_{nogrid}$ (air) of the pixel that radiation directly enters without transmitting through the subject S and the luminance value $I_{nogrid}$ (x, y) of the pixel that radiation transmitting through the subject S enters. Furthermore, the characteristics of the relationship between the thickness T of the subject S and the subject thickness index $\alpha$ (x, y), which is the signal reduction rate of radiation, is used for the acquired approximate thickness T of the subject S such that the signal reduction rate $D_{scat}$ of radiation can be acquired. Therefore, the luminance value $I_{real}$ can be calculated using the signal reduction rate $D_{scat}$ of radiation with respect to the approximate thickness T (ave) of the subject S actually imaged. That is, the luminance value $I_{real}$ based on the actually captured radiation image $X_{nogrid}$ can be calculated. Furthermore, the adjustment coefficient $I_{ideal}/I_{real}$ for adjusting the deviation between the luminance value $I_{real}$ based on the actually captured radiation image and the ideal luminance value $I_{ideal}$ uniquely determined under the specific imaging conditions can be acquired.

According to this embodiment, as described above, the image processor 6 is configured to calculate $D_{prim}$ based on the ratio of the luminance value $I_{grid}$ (air) of the non-subject region in the radiation image $X_{grid}$ captured in advance with the grid 8 being arranged to the luminance value $I_{nogrid}$ (air) of the non-subject region in the radiation image $X_{nogrid}$ captured without the grid 8 being arranged. Accordingly, the value of $D_{prim}$, which is the signal reduction rate due to passage of the radiation through the grid 8 (transmitters 8b), can be automatically obtained based on the image $X_{nogrid}$ actually captured without the user input. Consequently, it is possible to save the trouble of inputting.

According to this embodiment, as described above, the image processor 6 is configured to calculate $D_{scat}$ (x, y) based on the ratio of the luminance value $I_{nogrid}$ (x, y) of each pixel to the luminance value $I_{nogrid}$ (air) of the non-subject region in the radiation image $X_{nogrid}$ captured without the grid 8 being arranged. Accordingly, the value of $D_{scat}$ (x, y), which is the signal reduction rate due to removal of the scattered components in the subject S, can be automatically obtained based on the luminance value $I_{nogrid}$ (x, y) and the luminance value $I_{nogrid}$ (air) of the image $X_{nogrid}$ actually captured without the user input. Consequently, it is possible to save the trouble of inputting.

According to this embodiment, as described above, the image processor 6 is configured to calculate the subject thickness index $\alpha$ (x, y) corresponding to the thickness T of the subject S based on the above formula (6). Accordingly, the subject thickness index $\alpha$ (x, y) corresponding to the thickness T of the subject S can be easily acquired from the radiation image $X_{nogrid}$ (pixel luminance value $I_{nogrid}$ (x, y)) without measuring the actual thickness T of the subject S.

[Modified Examples]

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the correspondence relationship between the scattered dose Q and the thickness T used to acquire $I_{ideal}$ is acquired from the correspondence between the thickness T of the subject S and the scattered dose Q obtained from the measured luminance value when an acrylic plate or a phantom (human phantom) is defined in advance as the subject S, for example has been shown in the aforementioned embodiment, the present invention is not limited to this. In the present invention, the correspondence relationship between the scattered dose Q and the thickness T may be used as a correspondence relationship described in publicly known papers, for example. Furthermore, although the example in which the correspondence relationship is stored as a data table has been shown, the correspondence relationship may be stored as function data approximated by an appropriate function such as a trigonometric function.

While the example in which $I_{grid}$ (air) ($I_{nogrid}$ (air)) is acquired by averaging the luminance values of the regions of the radiation image $X_{nogrid}$ in which the luminance values exceed a predetermined threshold has been shown in the aforementioned embodiment, the present invention is not limited to this. In the present invention, when a ratio of the non-subject region is large to some extent, $I_{grid}$ (air) ($I_{nogrid}$ (air)) may be acquired from the local maximum value (mode) or the median value based on the luminance histogram of the radiation image $X_{nogrid}$. Furthermore, when an imaging region of the subject S is known, $I_{grid}$ (air) ($I_{nogrid}$ (air)) may be acquired from the luminance value of a pixel in the region corresponding to the non-subject region. For example, when the chest is imaged, the subject S is often imaged with the arms open to the left and right and spaced apart from the body side. Therefore, lower left and right regions (regions corresponding to the armpits) of the image are non-subject regions corresponding to incident radiation that does not transmit through the subject S. When the subject S is placed at the center and imaged, the edge of the image becomes a non-subject region. Alternatively, $I_{grid}$ (air) ($I_{nogrid}$ (air)) may be obtained from one luminance value (a maximum value in the image, for example). Alternatively, $I_{grid}$ (air) ($I_{nogrid}$ (air)) may be calculated by a statistical method for another luminance value.

While the example in which $D_{prim}$ is acquired from the luminance value $I_{nogrid}$ (air) of the non-subject region of the radiation image $X_{nogrid}$ and the luminance value $I_{grid}$ (air) of the non-subject region of the radiation image $X_{grid}$ has been shown in the aforementioned embodiment, the present invention is not limited to this. In the present invention, the signal reduction rate $D_{prim}$ due to passage through the grid may be stored for each grid to be used at the time of manufacturing the device, at the time of shipment, or at the time of the previous scattered ray removal process, for example. Thus, it is possible to acquire $D_{prim}$ by specifying the preset type of a grid to be used before imaging.

While the example in which the subject S is a human body has been shown in the aforementioned embodiment, the subject S may be an animal other than the human body or a non-living material.

While the scattered ray removal process operations of the image processor 6 are described using a flowchart in a "flow-driven manner" for the convenience of illustration in the aforementioned embodiment, the present invention is not limited to this. The process operations of the image processor 6 may be performed in an "event-driven manner" in which the process operations are performed on an event basis. In this case, the process operations may be performed in a complete event-driven manner or in a combination of an event-driven manner and a flow-driven manner.

DESCRIPTION OF REFERENCE NUMERALS

6: image processor
7: storage (database unit)
8: grid
100: radiation image processing device

The invention claimed is:

1. A radiation image processing method comprising:
    storing a signal reduction rate of radiation due to a scattered ray generated by the radiation transmitting through a subject, and a correspondence relationship between a thickness of the subject and a scattered dose;
    calculating an ideal luminance value in accordance with the correspondence relationship;
    capturing an actual radiation image without using a grid configured for removing a scattered ray therefrom;
    calculating an actual luminance value for the radiation image in accordance with the signal reduction rate;
    calculating an adjustment coefficient by calculating a ratio of the ideal luminance value to the actual luminance value; and
    removing a signal component of the scattered ray superimposed on the
    actual captured radiation image based on the calculated adjustment coefficient.

2. The radiation image processing method according to claim 1, wherein the removing the signal component of the scattered ray includes removing the signal component of the scattered ray superimposed on the radiation image captured without the grid being arranged, and calculating a luminance value $I_{est}$ (x, y) estimated assuming that the grid is arranged based on a following formula (1):

$$I_{est}(x, y) = I_{nogrid}(x, y) \times D_{prim} \times \frac{I_{ideal}}{I_{real}} \times D_{scat}, \qquad (1)$$

$$(0 \le D_{prim} \le 1, 0 \le D_{scat} \le 1)$$

where $I_{nogrid}$ (x, y) represents a luminance value at coordinates (x, y) of the radiation image captured without the grid being arranged, the radiation image containing the signal of the scattered ray, $D_{prim}$ represents a signal reduction rate due to passage through the grid, $D_{scat}$ represents the signal reduction rate of the radiation stored in a database unit, $I_{ideal}$ represents the ideal luminance value under a specific imaging condition, and $I_{real}$ represents the luminance value based on the radiation image actually captured, and $I_{ideal}/I_{real}$ represents the adjustment coefficient.

3. The radiation image processing method according to claim 2, wherein
    the storing the signal reduction rate of the radiation and the correspondence relationship between the thickness of the subject and the scattered dose includes storing a characteristic of a relationship between the thickness of the subject corresponding to a reduction rate of a luminance value of a pixel corresponding to a subject region in which the radiation transmits through the subject with respect to a luminance value of a pixel corresponding to a non-subject region in which the radiation does not transmit through the subject in the radiation image captured without the grid being arranged, and a signal reduction rate due to removal of a scattered component; and the removing the signal component of the scattered ray includes calculating the $I_{real}$ based on the stored characteristic of the relationship between the thickness of the subject and the signal reduction rate of the radiation, and the luminance value of the radiation image actually captured.

4. The radiation image processing method according to claim 3, wherein the removing the signal component of the scattered ray includes calculating the $D_{prim}$ based on a ratio of a luminance value of the non-subject region in the radiation image captured in advance with the grid being arranged to a luminance value of the non-subject region in the radiation image captured without the grid being arranged.

5. The radiation image processing method according to claim 4, wherein the removing the signal component of the scattered ray includes calculating the $D_{scat}$ based on a ratio of a luminance value of each pixel to a luminance value of the non-subject region in the radiation image captured without the grid being arranged.

6. The radiation image processing method according to claim 5, wherein the removing the signal component of the scattered ray includes calculating a subject thickness index corresponding to the thickness of the subject based on a following formula (2):

$$\left(1 - \frac{I_{nogrid}(x, y)}{I_{nogrid}(\text{air})}\right) \tag{2}$$

where $I_{nogrid}$ (air) represents the luminance value of the non-subject region in the radiation image captured without the grid being arranged.

7. The radiation image processing method according to claim 1, wherein calculating the actual luminance includes using a value of Dprim as well as the signal reduction rate for the calculation, the value of Dprim being a ratio of a luminance value of a non-subject region in the radiation image captured in advance with the grid being arranged to a luminance value of the non-subject region in the radiation image captured without the grid being arranged.

* * * * *